(12) United States Patent
Bor (10) Patent No.: US 11,950,845 B2
(45) Date of Patent: Apr. 9, 2024

(54) SYSTEM AND METHODS FOR IDENTIFICATION OF THE HUMAN VISUAL AXIS

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 552 days.

(21) Appl. No.: 17/225,217

(22) Filed: Apr. 8, 2021

(65) Prior Publication Data

US 2021/0321869 A1 Oct. 21, 2021

Related U.S. Application Data

(60) Provisional application No. 63/010,293, filed on Apr. 15, 2020.

(51) Int. Cl.
| | |
|---|---|
| *A61B 3/103* | (2006.01) |
| *A61B 3/00* | (2006.01) |
| *A61B 3/14* | (2006.01) |
| A61B 3/024 | (2006.01) |

(52) U.S. Cl.
CPC ............ *A61B 3/103* (2013.01); *A61B 3/0025* (2013.01); *A61B 3/0091* (2013.01); *A61B 3/14* (2013.01)

(58) Field of Classification Search
CPC ....... A61B 3/024; A61B 3/103; A61B 3/0025; A61B 3/0091; A61B 3/14; A61B 3/113

USPC ................ 351/200, 205, 206, 208
See application file for complete search history.

(56) References Cited

U.S. PATENT DOCUMENTS

| | | | | |
|---|---|---|---|---|
| 5,237,351 A | * | 8/1993 | Kohayakawa | A61B 3/103 351/243 |
| 6,036,316 A | * | 3/2000 | Arita | A61B 3/113 351/212 |
| 2007/0285620 A1 | | 12/2007 | Clark | |

FOREIGN PATENT DOCUMENTS

WO 2006101656 A2 9/2006

* cited by examiner

*Primary Examiner* — Tuyen Tra (57) ABSTRACT

The present disclosure generally relates to methods and apparatus for accurate identification of the visual axis of the eye. In one embodiment, a visual axis identification system includes a fixation light source, a camera, a processing system, and a multifocal lens. The patient focuses their gaze through the multifocal lens and onto a fixation light beam provided by the fixation light source. The passage of the fixation light beam through the multifocal lens creates two or more images on or near to the patient's retina. The multifocal lens and/or the patient's eye are then moved relative to each other while the patient continuously maintains their gaze on the fixation light beam. The patient's visual axis may be located by determining the location of the optical center of the multifocal trial lens relative to the patient's eye when the centers of the multiple images coincide on the retina.

15 Claims, 13 Drawing Sheets

SYSTEM AND METHODS FOR IDENTIFICATION OF THE HUMAN VISUAL AXIS

BACKGROUND

Field

Embodiments of the present disclosure generally relate to methods and apparatus for vision characterization, and more particularly, to methods and apparatus for accurate identification of the visual axis of the eye.

Description of the Related Art

Conventional techniques for presbyopic treatment typically include determining the relative location of the visual axis of each of the patient's eyes. Accurate determination of these axes is essential for effective placement of small-area bifocal, multifocal, and extended depth of focus (EDOF) intraocular lenses (IOLs). Even a slight misalignment of these lenses may significantly impede any benefits intended by surgical implantation thereof. Other examples of presbyopic treatments that may also benefit from the determination of the visual axis include LASIK, PresbyLASIK or multifocal LASIK, and photorefractive keratectomy (PRK) surgery, to name a few.

The visual axis is one's actual line of sight, which is a straight line joining the fovea of the eye, a small depression in the retina and the clearest point of vision, with a fixation point in the patient's visual field. Thus, measuring the visual axis is essential for determining the placement of bifocal and multifocal lenses as the viewing areas of such lenses are narrow and even a slight misalignment may significantly impede their function. Currently, there are no diagnostic devices for accurately and precisely determining the location of the visual axis. Instead, the location of the visual axis is generally approximated to be halfway between the optical axis and the corneal vertex, or first Purkinje image, which is the reflection of a fixation light on the outer surface of the cornea. This method is frequently inaccurate, as the visual axis can be located far away from the aforementioned halfway point (e.g., especially in compromised or unusually shaped eyes).

Accordingly, what is needed in the art are improved methods and apparatus for identifying the visual axis of the eye.

SUMMARY

The present disclosure generally relates to methods and apparatus for accurate identification of the visual axis of the eye.

In certain embodiments, a method for determining a location of a visual axis of a patient's eye is provided. The method includes placing a multifocal optical lens adjacent to the patient's eye, wherein the multifocal optical lens includes two or more optical powers with corresponding and spatially coinciding optical centers at an optical center of the multifocal optical lens. A fixation light beam is generated and directed towards the patient's eye, which forms two or more images near the patient's retina that correspond with the two or more optical powers of the multifocal lens. The method further includes capturing images of the patient's eye and the optical lens along a direction of the fixation light beam and determining an X/Y location of the patient's eye relative to an X/Y location of the optical center of the multifocal optical lens. The multifocal optical lens is moved along an X/Y direction while the patient maintains their gaze on the fixation light until centers of the two or more images coincide in the patient's view. At that point, the location of the visual axis of the patient's eye is detected and located at a pupil plane of the patient's eye, the location of visual axis corresponding with a location of the optical center of the multifocal optical lens as viewed from the direction of the fixation light beam.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to methods and apparatus for accurate identification of the visual axis of the eye. In certain embodiments, a visual axis identification system includes a fixation light source, a camera, a processing system, and a multifocal lens. The multifocal lens may be coupled to a trial frame to be worn by a patient or to an off-patient device. In determining the location of the visual axis of the patient, the patient focuses their gaze through the multifocal lens onto a fixation light beam provided by the fixation light source. The passage of the fixation light beam through the multifocal lens creates two or more images on or near the patient's retina. The multifocal lens and/or the patient's eye are then moved relative to one another while the patient continuously maintains their gaze on the fixation light beam. The patient's visual axis may be located by determining the location of the optical center of the multifocal trial lens relative to the patient's eye when the centers of the multiple images coincide on the retina.

Figure 1:
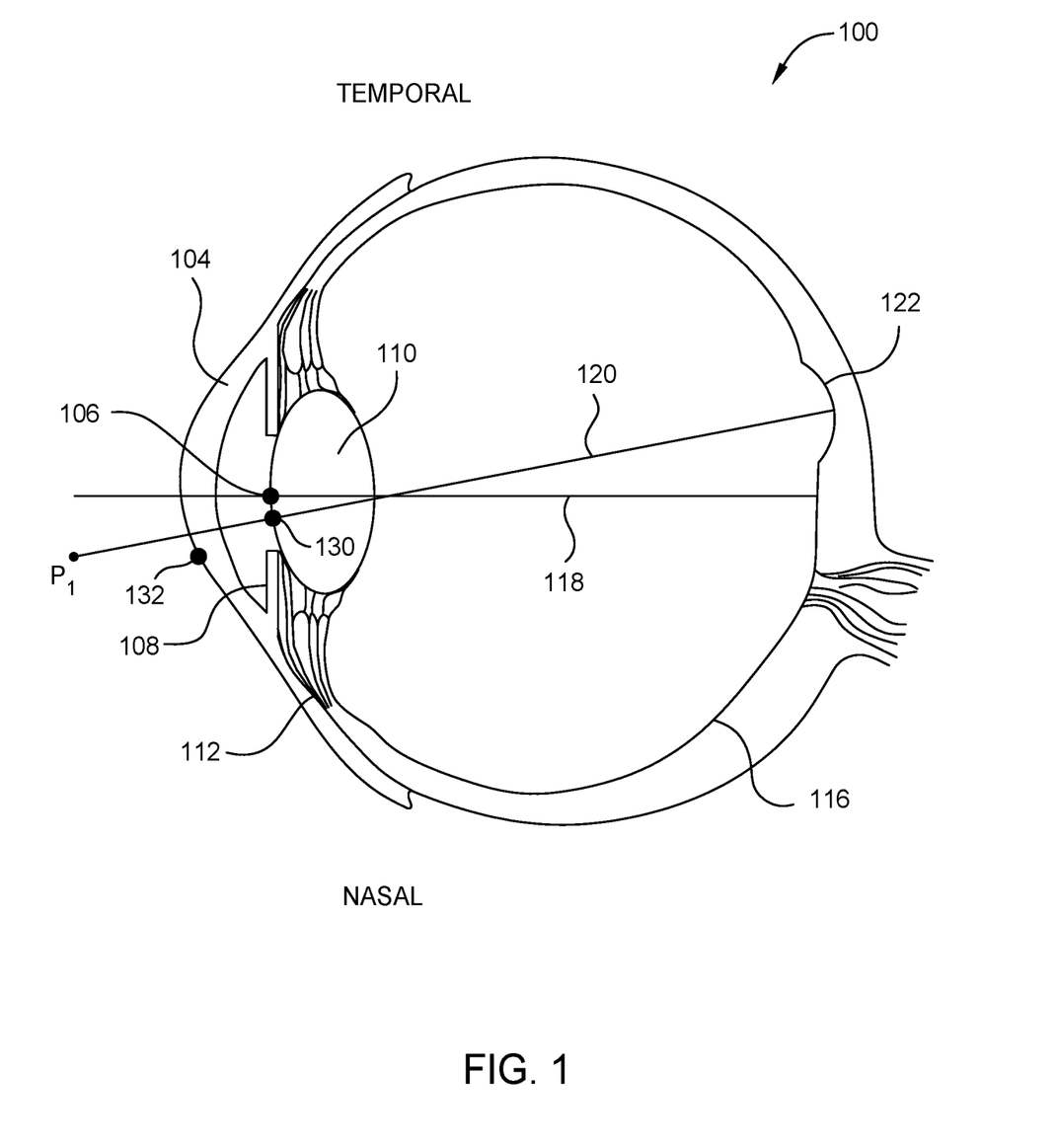
FIG. 1 illustrates a cross-sectional top view of a human eye.

FIG. 1 illustrates a simplified cross-sectional top view of an exemplary human eye 100. The temporal and nasal sides of the eye 100 are depicted in FIG. 1 for reference. In general, the eye 100 includes a cornea 104, a pupil whose center 106 is shown, an iris 108, a natural lens 110, ciliary muscle 112, and a retina 116. A pupillary axis 118 is perpendicular to a plane of the iris 108 and passes through the pupillary center 106.

FIG. 1 further depicts a visual axis 120 from a fixation point Pi through the cornea 104 and the pupil to a fovea 122, which refers to a small depression in the retina 116. The center of the field vision is focused in the fovea 122 where retinal cones are particularly concentrated and thus, visual acuity is highest along the visual axis 120. Accordingly, accurate determination of a location 130 of the visual axis 120 is essential for successful alignment of bifocal or multifocal corrective lenses. The location 130 of the visual axis 120 refers to an X/Y position or location of a point on a plane of the iris 108 or the pupil plane through which the visual axis 120 passes. As described earlier, however, there are presently no ophthalmic diagnostic devices that can precisely identify the location 130 of the visual axis 120.

Conventional ophthalmic techniques involve approximating the location 130 of the visual axis 120 as a halfway point between the pupillary center 106 and a corneal vertex 132, or first Purkinje image, which is defined as the location of the specular reflection from the anterior surface of the cornea 104 as seen from the direction of a fixation light source. Current approximation techniques may lead to ineffective or suboptimal corrective measures such as mispositioning of multifocal corrective lenses or presbyopic or PRK treatments. Embodiments of the present disclosure provide improved systems and methods for accurately locating the intersection of the visual axis 120 with the pupil plane of the eye (location 130). Accordingly, embodiments of the present disclosure may be utilized for corrective lens alignment as well as other ophthalmic procedures, including ophthalmic surgeries such as multifocal LASIK or multifocal PRK surgery.

Figure 2A:
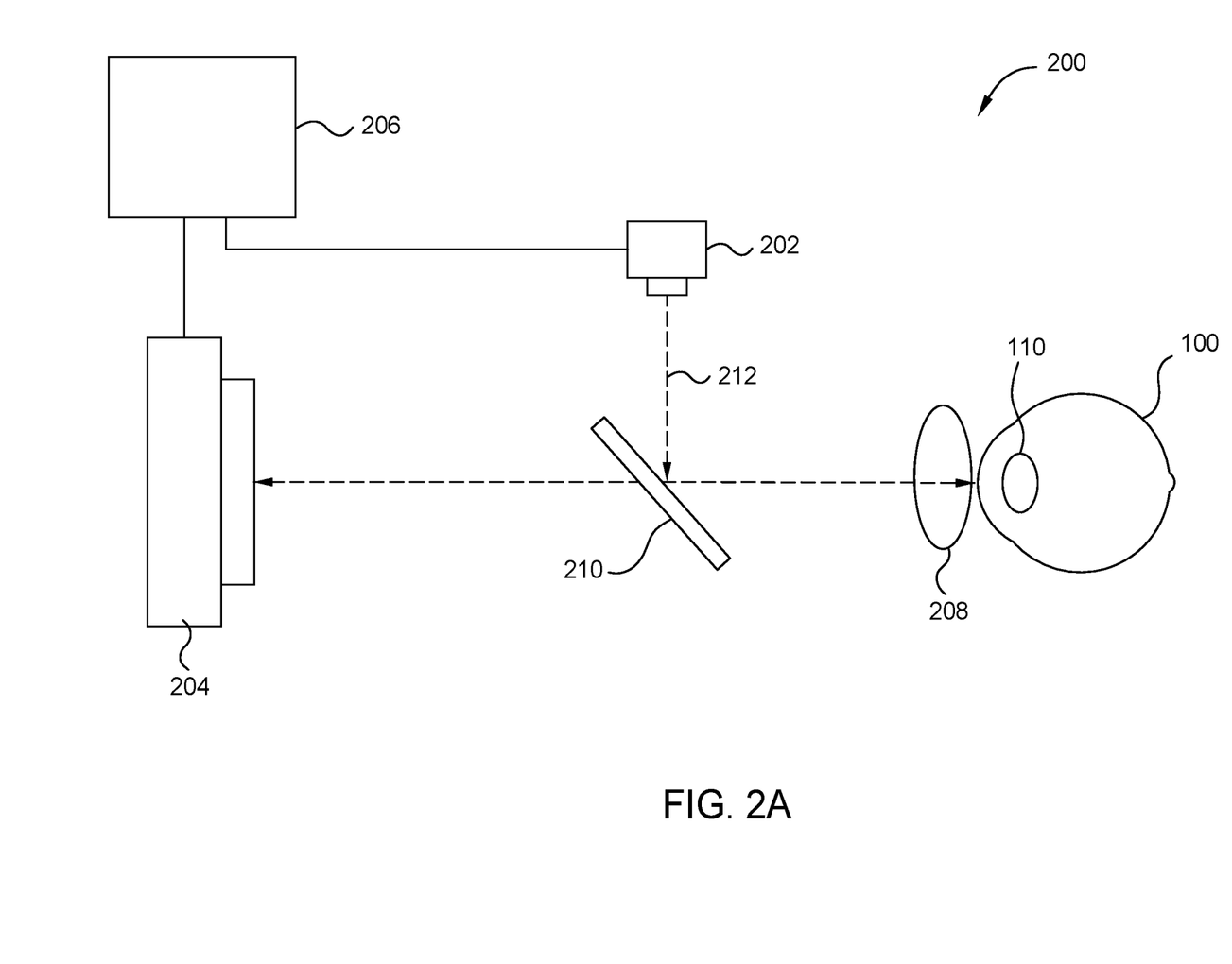
FIG. 2A illustrates a schematic diagram of a visual axis identification system according to certain embodiments of the present disclosure.

FIG. 2 illustrates a simplified schematic view of an exemplary visual axis identification system 200 according to some embodiments. The visual axis identification system 200 includes a fixation light source 202, an imaging camera 204, an image processing system 206, and a multifocal lens 208. Generally, the fixation light source 202 and one or more associated optical relay devices 210 are configured to provide a fixation light beam 212 to the eye 100. For example, the fixation light source 202 may include one or more light emitting diodes (LEDs) configured to emit the fixation light beam 212. Other examples of suitable light sources that may be utilized for the fixation light source 202 include filament lamps and the like. In some embodiments, the fixation light source 202 may provide a fixation light beam 212 having multiple wavelengths. The one or more optical relay devices 210 may include any suitable optical relay devices such as relay lenses, beam splitters, filters, and the like.

The imaging camera 204 may include any suitable digital imaging device or image detector, such as an eye tracking camera or similar optical sensor, for capturing images of and determining the location (e.g., X/Y translational position) of the eye 100 and the multifocal lens 208. In some embodiments, the imaging camera 204 is an infrared optical sensor configured to track the X/Y location of the eye 100 and the X/Y location of the multifocal lens 208. In such embodiments, the eye 100 is illuminated with an infrared fixation light source 202. In some embodiments, the imaging camera 204 is an optical sensor configured to track movement of the eye 100 by mapping and detecting shifts (e.g., movement) of the vasculature (e.g., blood vessels) within the eye 100, such as vasculature within the sclera which is the white outer layer of the eye 100.

The imaging camera 204 is communicatively coupled to the image processing system 206 and may form a single device therewith. For example, the imaging camera 204 and the image processing system 206 may be separate components within a single imaging device or system. Generally, the imaging camera 204 is configured to capture images of the eye 100 and transmit those images to the image processing system 206 for analysis during utilization of the visual axis identification system 200. The image processing system 206 is then configured to determine the X/Y location of the eye 100 as well as the X/Y location of the multifocal lens 208.

Figure 2B:
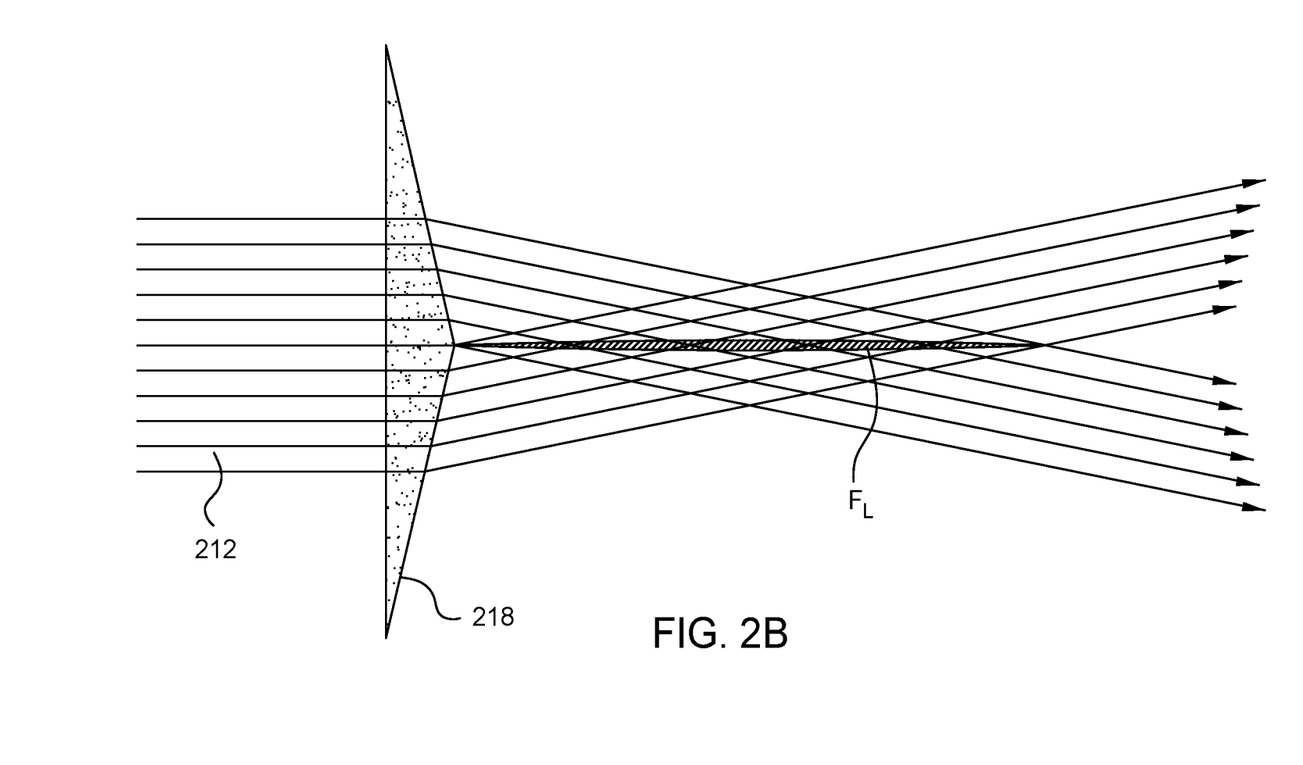
FIG. 2B illustrates a schematic diagram of an exemplary optical element for utilization with a visual axis identification system according to certain embodiments of the present disclosure.

The determination of the X/Y location of the eye 100 by the image processing system 206 is made relative to the X/Y location of the multifocal lens 208. The multifocal lens 208 may be any suitable type of multifocal optical lens. In certain embodiments, the multifocal lens 208 is a multifocal lens having two or more powers, such as a bifocal lens. In certain embodiments, the multifocal lens 208 is a multifocal lens having a reflective coating on two or more sides thereof. In further embodiments, the multifocal lens 208 includes a diffractive optical element, such as a holographic element, a Fresnel-type lens, or the like. In still further embodiments, the multifocal lens 208 includes an axicon or an aspheric extended depth of focus lens forming a long or hyper-long focal line (i.e., a Bessel beam) instead of a single focal point. An exemplary axicon 218 forming a hyper-long focal line $F_L$ is depicted in FIG. 2B. Also, note that although the multifocal lens 208 is presented with a certain oval shape, the multifocal lens 208 may have any suitable shape, such as the different shapes shown in the various Figures herein.

Examples of different types of multifocal lenses that can be used in the embodiments described herein are further described in more detail with respect to FIGS. 3A-3B, 4A-4C, and 6A-6D. For example, as depicted in FIGS. 3A-3B and 4A-4C, multifocal lens 308 includes at least two optical powers creating two different corresponding focal points: a first power 307 configured to correct the refractive error of the eye 100 for distance vision, and a second power 309 or "add power" for near vision. In certain embodiments, the first power 307 corresponds to one optical element or region while the second power 309 corresponds to a separate second optical element or region. Furthermore, the first power 307 and second power 309 have coinciding (e.g., overlapping) optical centers at an optical center 314 of the multifocal lens 308. Thus, it may be said that the first power 307 and the second power 309 share the optical center 314. In some embodiments, the second power 309 is provided by a refractive element having a diameter less than a diameter of the pupil, such as a diameter less than about 1.5 mm, and an optical power of about 2 diopter.

Figure 3A:
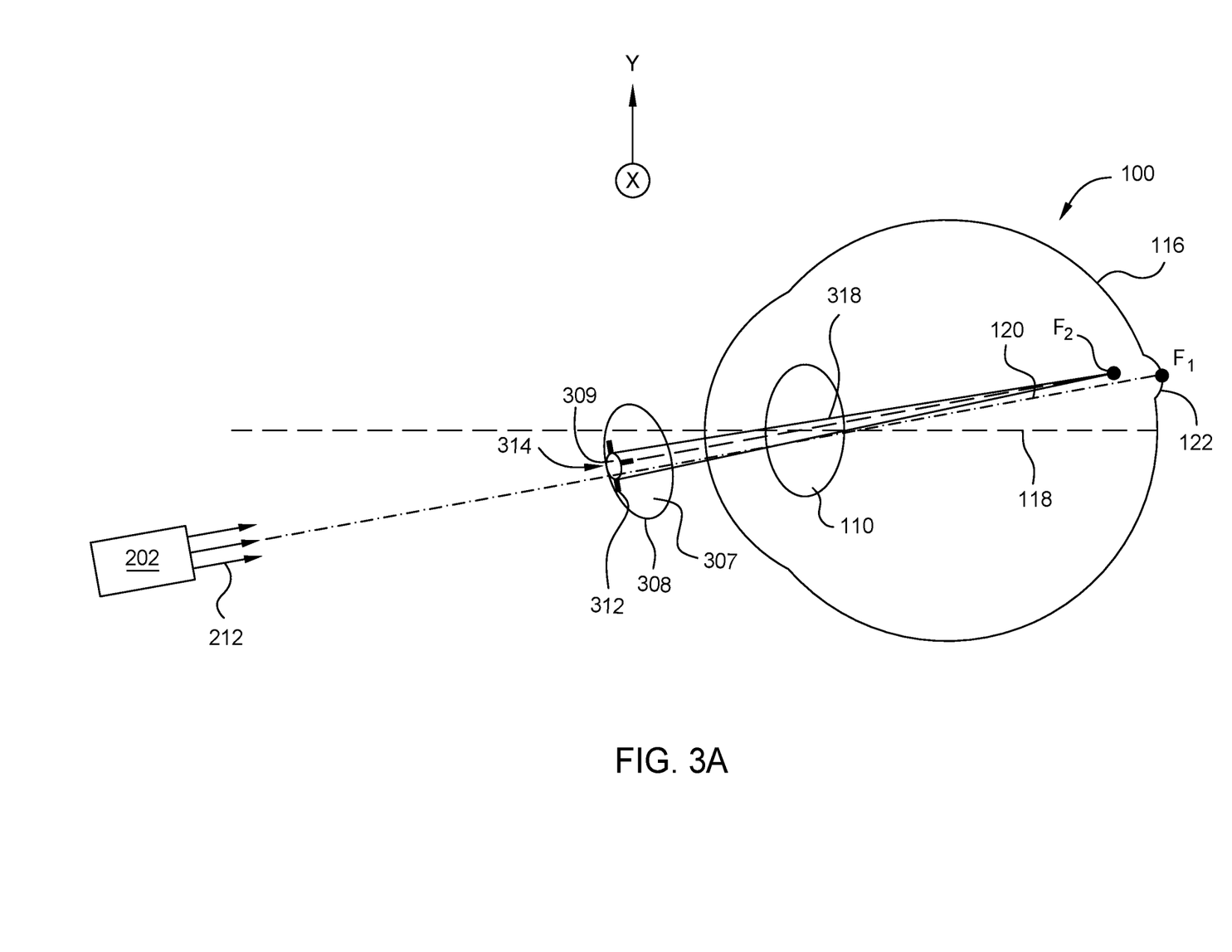
FIG. 3A illustrates a schematic diagram of a portion of a visual axis identification system according to certain embodiments of the present disclosure.
Figure 3B:
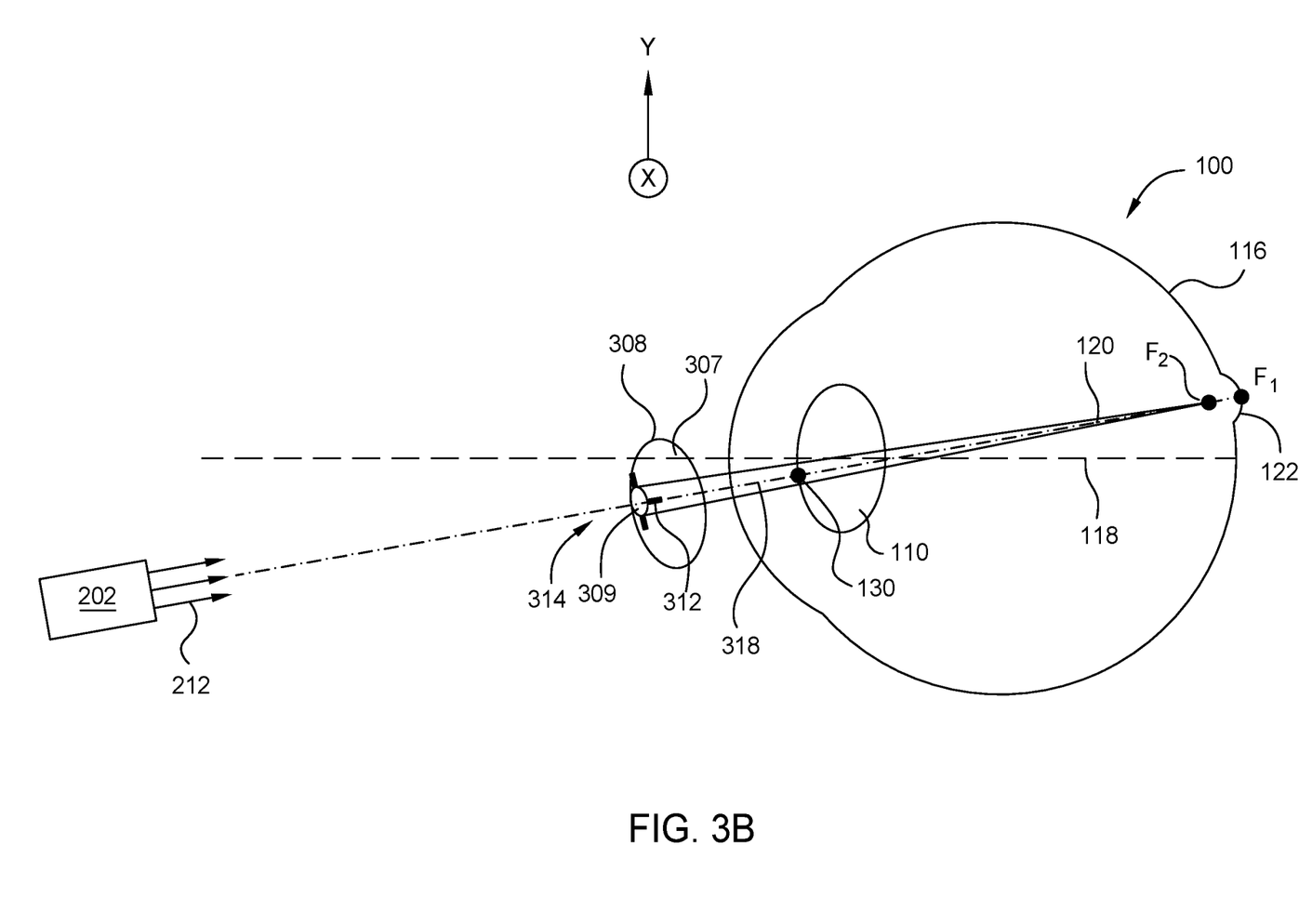
FIG. 3B illustrates a schematic diagram of a portion of a visual axis identification system according to certain embodiments of the present disclosure.

As shown in and described with respect to FIGS. 3A-3B, the multifocal lens 308 may be coupled (e.g., attached) to an off-patient device, such as an ophthalmic testing device, during utilization of the visual axis identification system 200. Thus, movement of the off-patient device causes displacement of the multifocal lens 308 relative to the eye 100 of the patient. Alternatively, the multifocal lens 308 may be coupled to a trial frame 440, shown in FIGS. 4A-4C, to be worn by a patient. Accordingly, rotation of the patient's head while the patient wears the trial frame 440 causes shifting of the multifocal lens 308 relative to the eye 100, and the shifting is proportional to a distance between the multifocal lens 308 and the eye 100 as well as the angle of rotation of the patient's head. In further embodiments, the optical center of the multifocal lens 308 includes markings 312, such as crosshair markings, to identify the optical center of the multifocal lens 308 for easier locating thereof.

In another example depicted in FIGS. 6A-6D, the multifocal lens 608 includes a reflective coating 603 formed on opposing sides thereof. The coating 603 thus replaces the functions of the powers 307 and 309, creating a plurality of focal points with the light passed through the multifocal lens 608. Similar to the multifocal lens 308, the multifocal lens 608 may be coupled to an off-patient device or a trial frame during use thereof.

Figure 4A:
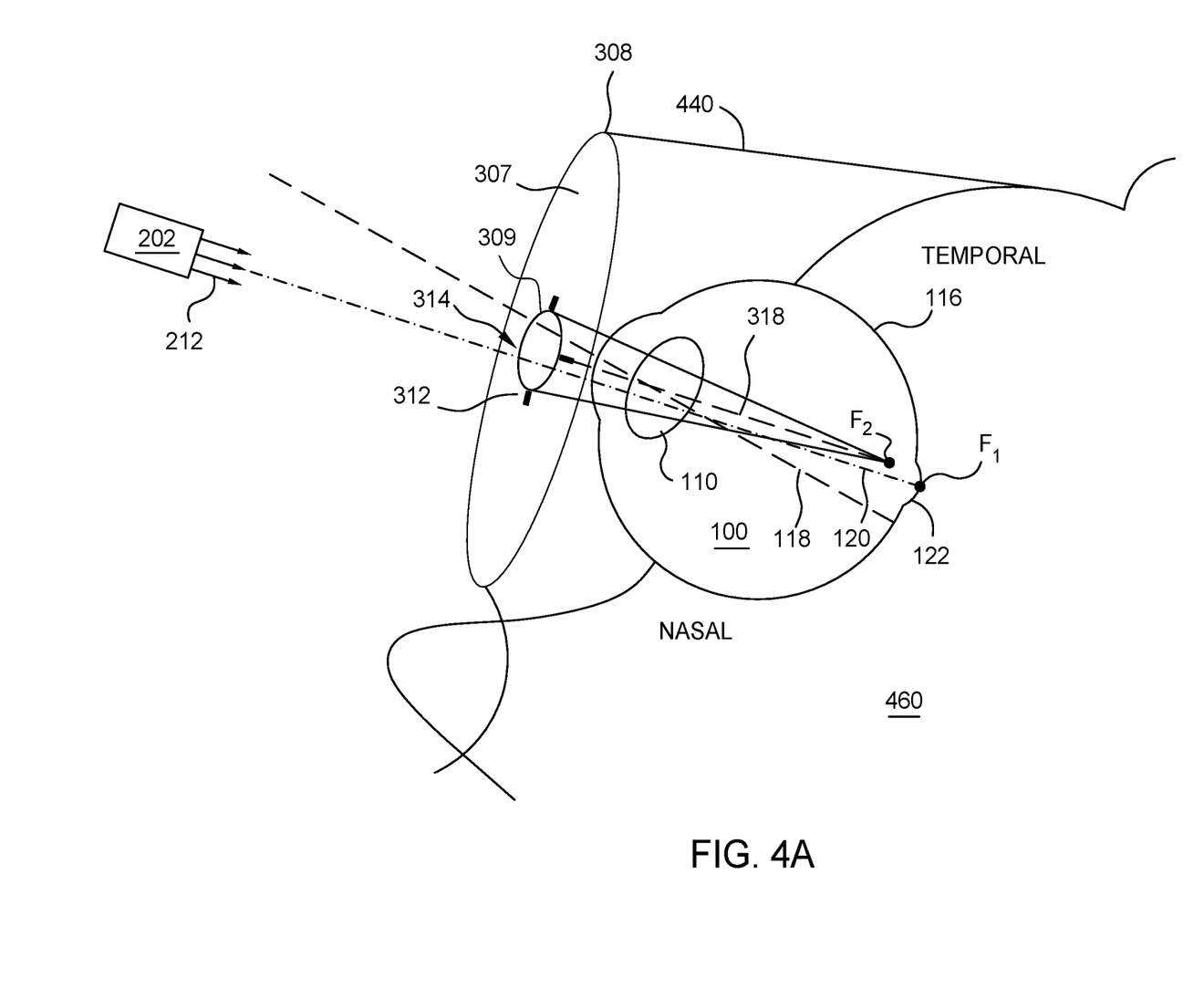
FIG. 4A illustrates a schematic top view of a portion of a visual axis identification system according to certain embodiments of the present disclosure.
Figure 4B:
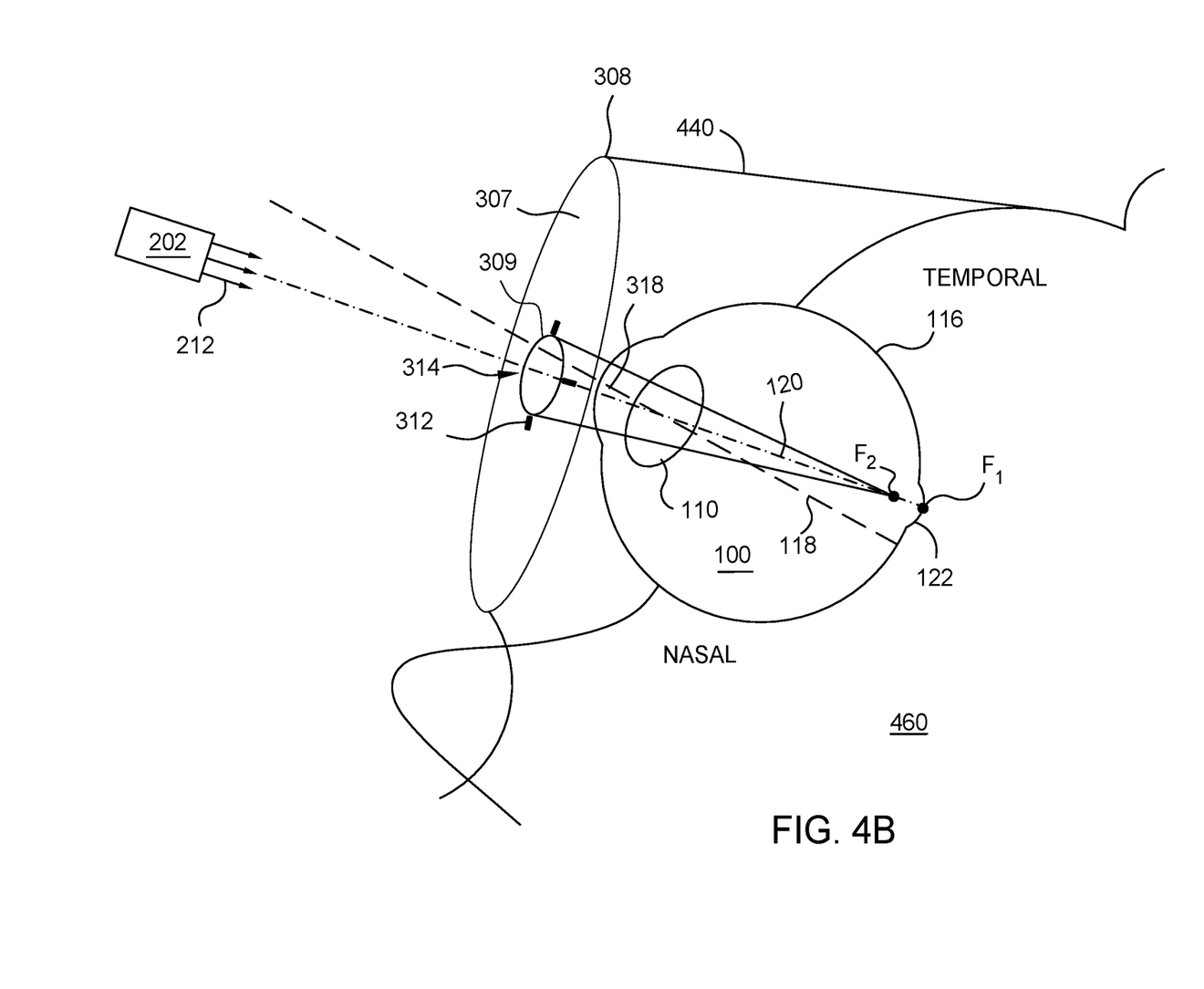
FIG. 4B illustrates a schematic top view of a portion of a visual axis identification system according to certain embodiments of the present disclosure.
Figure 4C:
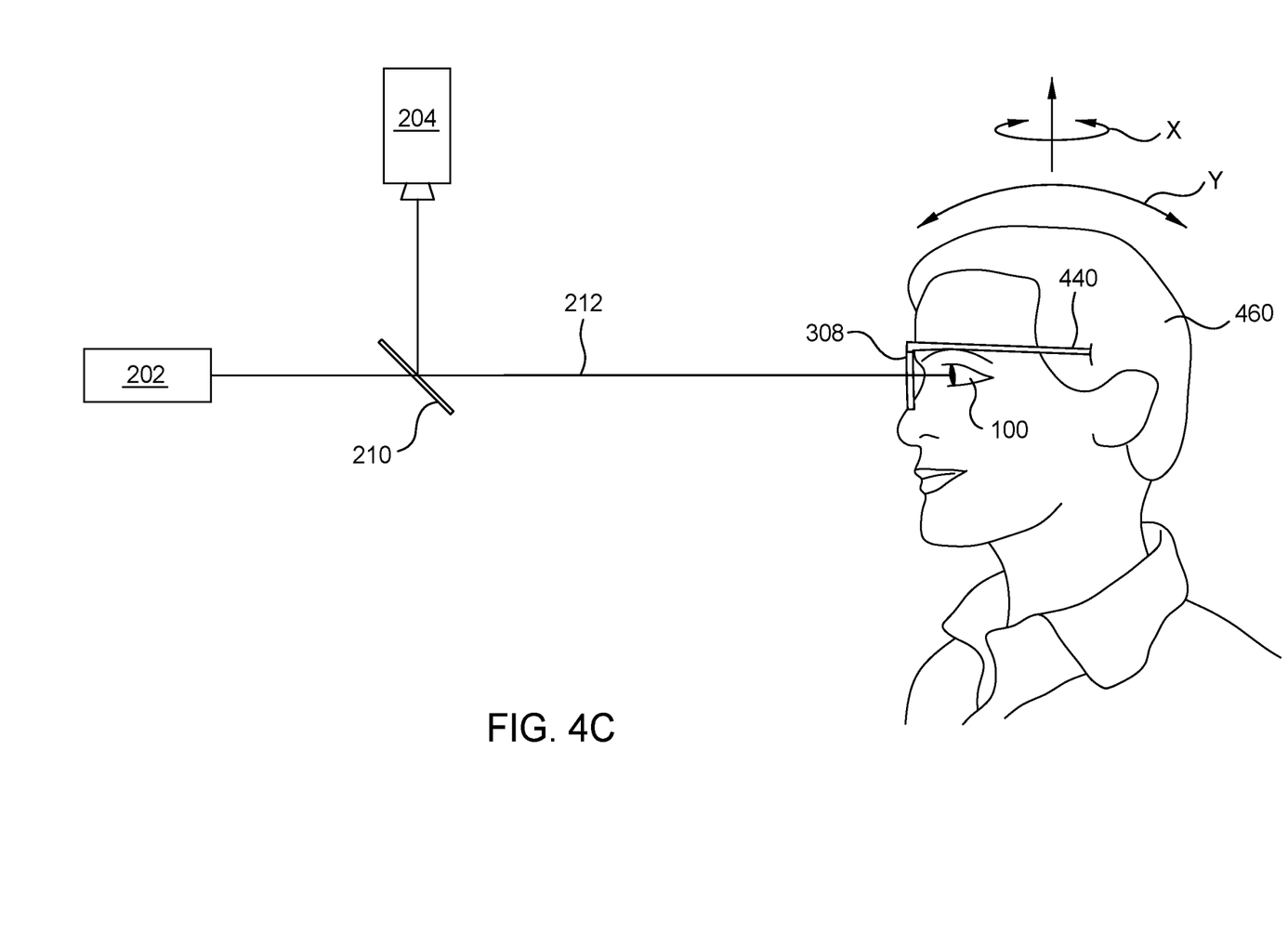
FIG. 4C illustrates a schematic side view of a portion of a visual axis identification system according to certain embodiments of the present disclosure.
Figure 5:
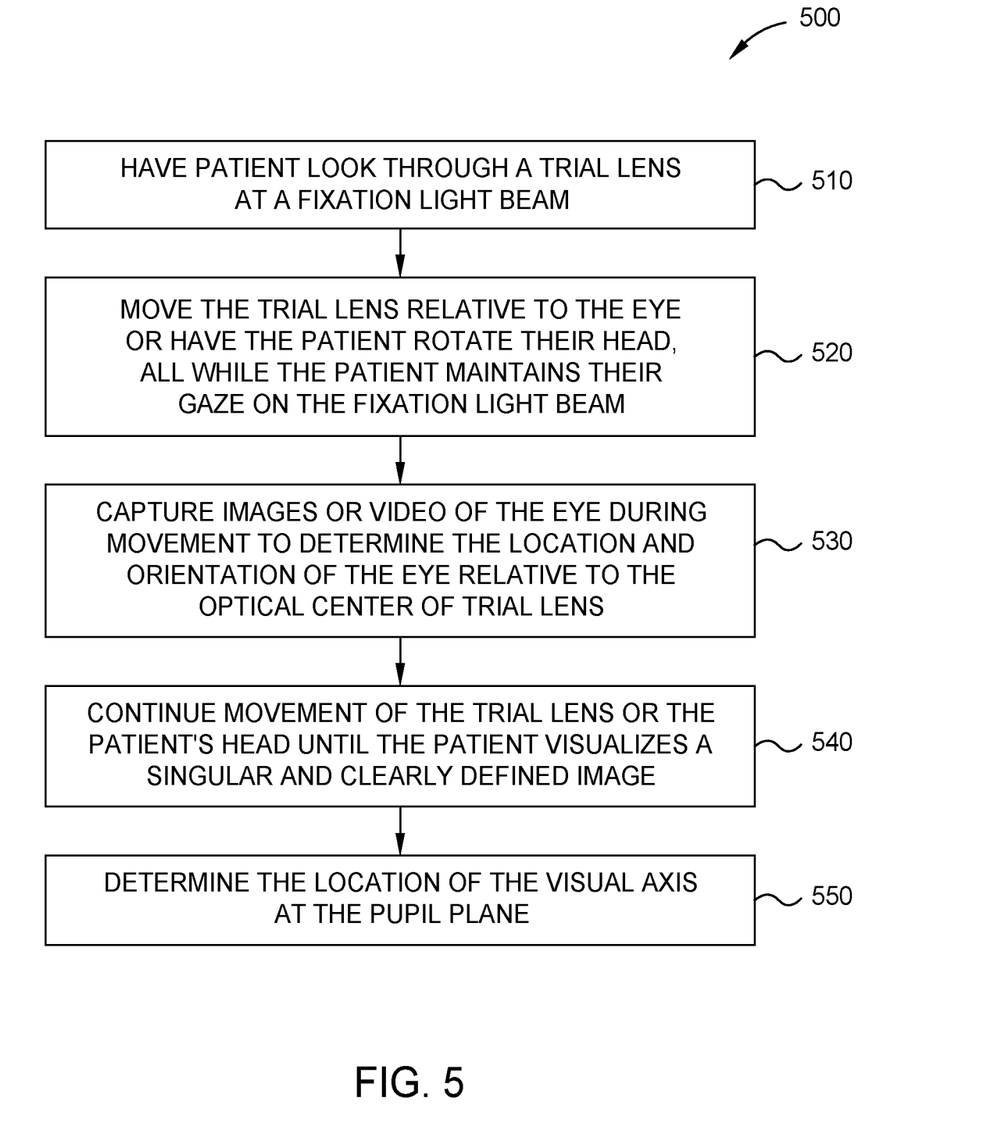
FIG. 5 illustrates a block diagram of a method for using the visual axis identification system of FIGS. 2, 3A, 3B, and 4A-4C according to certain embodiments of the present disclosure.
Figure 6A:
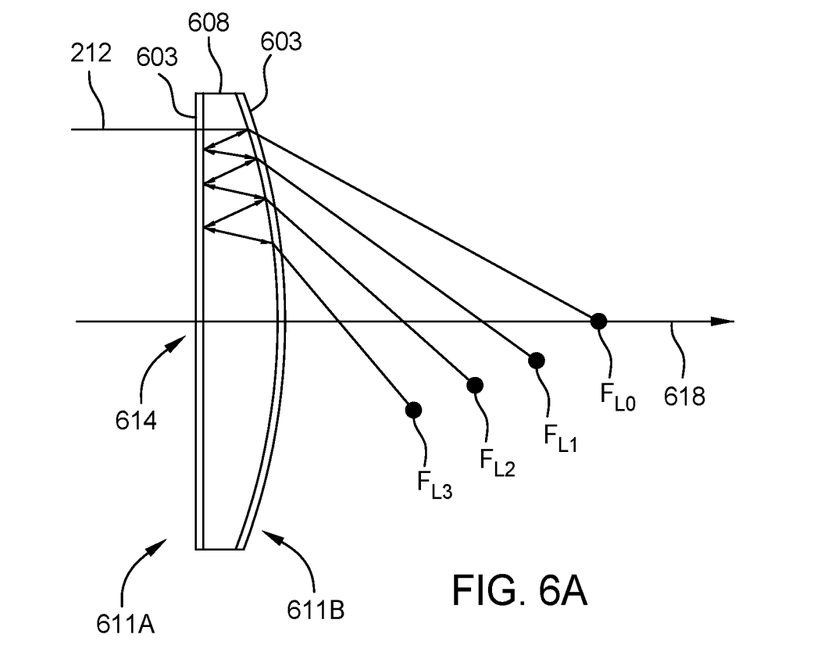
FIG. 6A illustrates a schematic diagram of a portion of a visual axis identification system according to certain embodiments of the present disclosure.
Figure 6B:
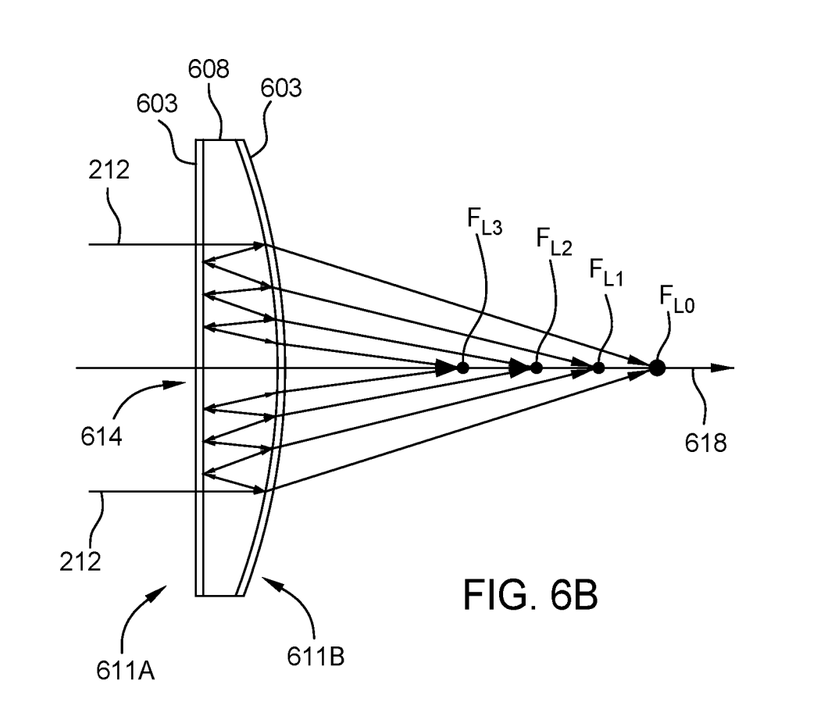
FIG. 6B illustrates a schematic diagram of a portion of a visual axis identification system according to certain embodiments of the present disclosure.
Figure 6C:
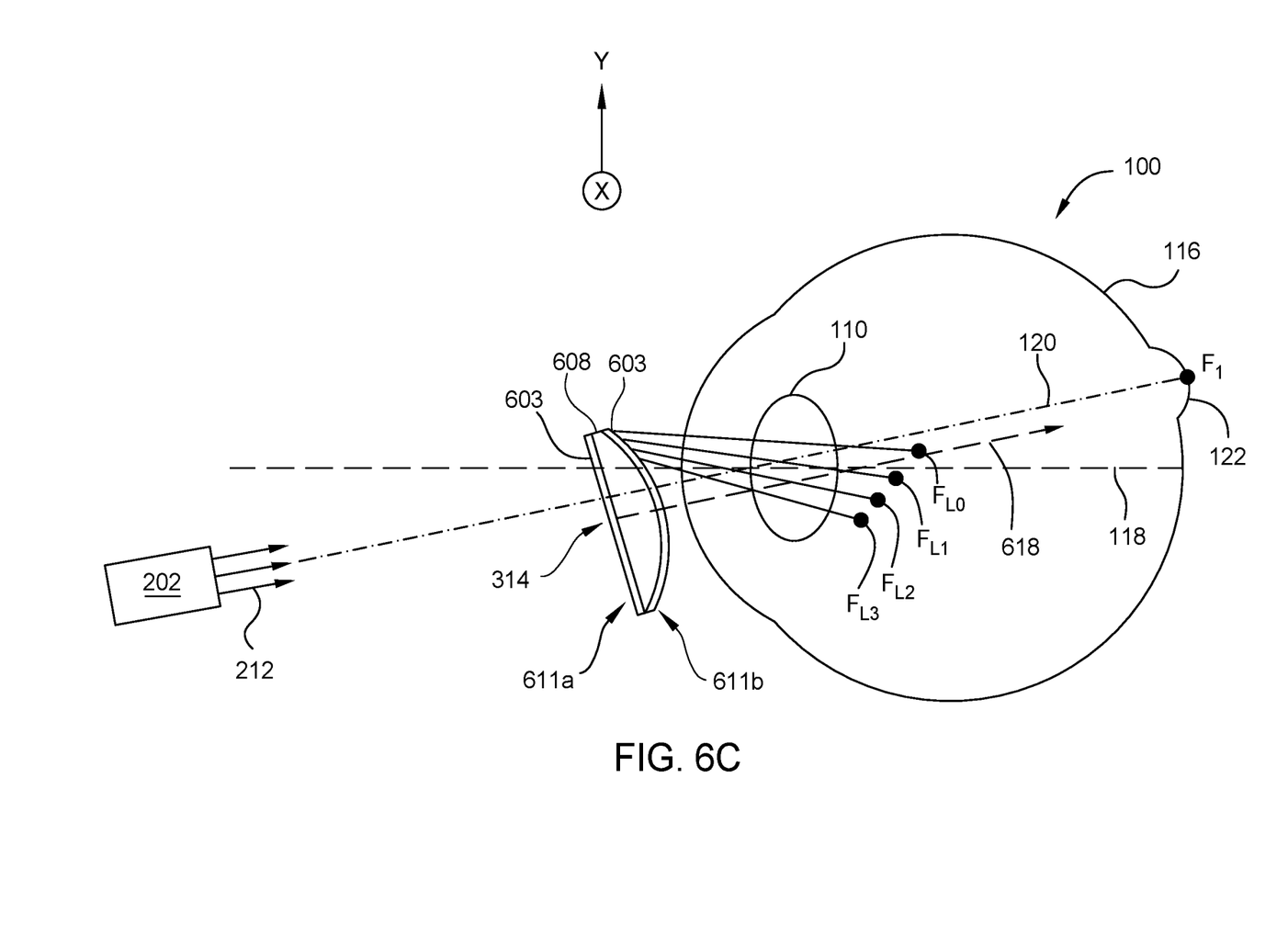
FIG. 6C illustrates a schematic diagram of a portion of a visual axis identification system according to certain embodiments of the present disclosure.
Figure 6D:
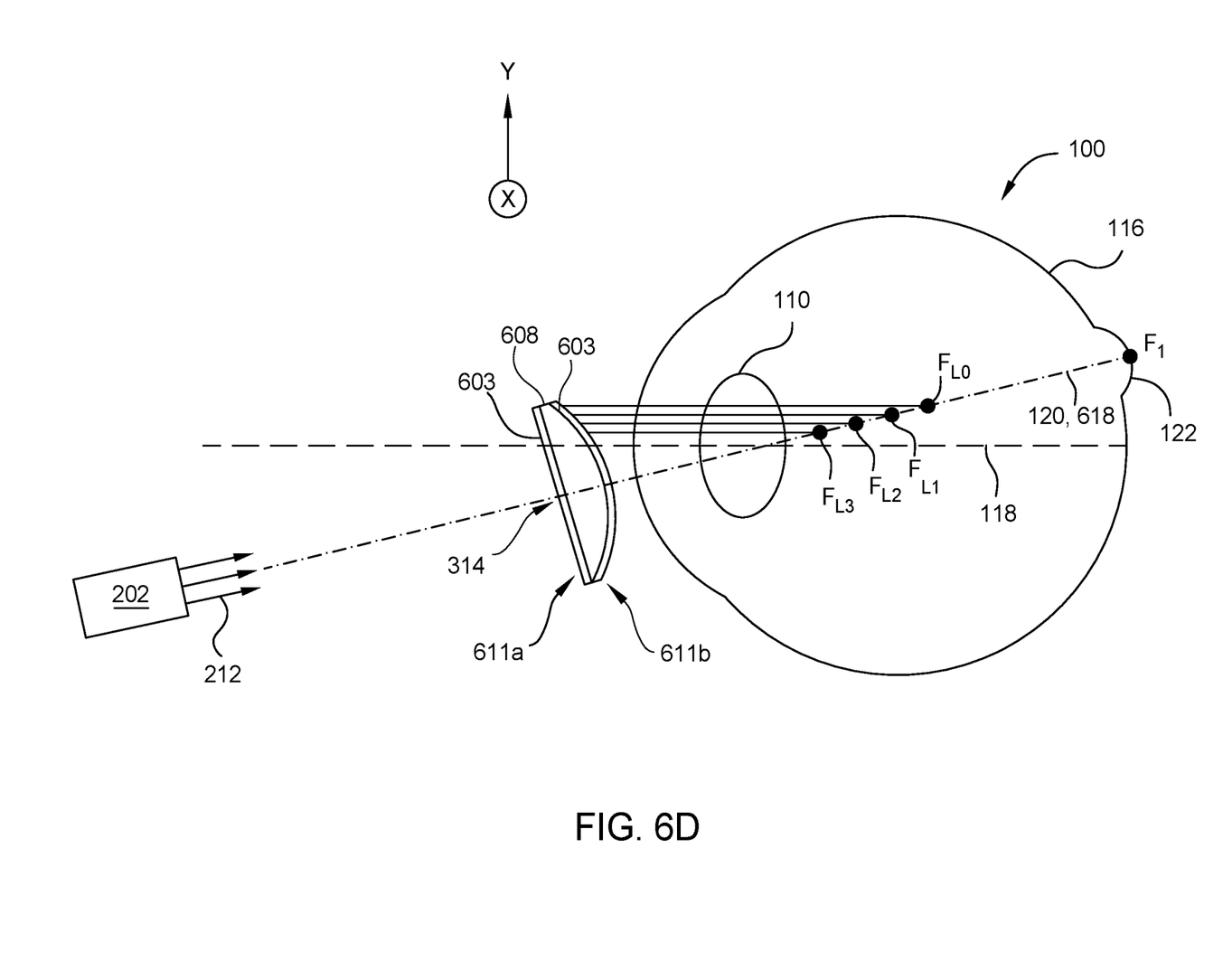
FIG. 6D illustrates a schematic diagram of a portion of a visual axis identification system according to certain embodiments of the present disclosure.

As previously described, FIGS. 3A and 3B illustrate simplified schematic views of the multifocal lens 308 when utilized with an off-patient device, while FIGS. 4A-4C illustrate simplified schematic top and side views of the multifocal lens 308 being worn by a patient in the trial frame 440, according to certain embodiments. FIG. 5 illustrates a flow diagram of a method 500 for determining the location 130 of the visual axis 120 with the visual axis identification system 200 of FIG. 2, which may include the multifocal lens 308 coupled to an off-patient device or the trial frame 440 according to some embodiments. Accordingly, FIGS. 3A, 3B, and 4A-4C will be herein described in more detail together with FIG. 5 for clarity.

Generally, while using the visual axis identification system 200, the patient looks through the multifocal lens 308 and focuses their gaze on the fixation light beam 212 at operation 510. As the patient focuses their gaze on the fixation light beam 212, a focal point F1 is formed on the fovea 122, where the center of the patient's field of vision is located. The second power 209 of the multifocal lens 308 also creates a second focal point $F_2$ near the retina 116 and along an optical axis 318 of the multifocal lens 308. The focal point $F_2$ has a different lateral location than the focal point $F_1$ located on the retina 116 due to the increased focusing (e.g., converging) of light rays in the fixation light beam 212 by the second power 209 of the multifocal lens 308 having, for example, a positive diopter.

When the focal point $F_1$ and the focal point $F_2$ are not aligned (e.g., not overlapping or transversally shifted with respect to each other) along the visual axis 120 as depicted in FIGS. 3A and 4A, two isolated (e.g., unaligned, non-overlapping) images are formed on the retina 116 of the patient. Under these circumstances, the patient may visualize two "spots" formed by the fixation light beam 212: a first sharp image created by the focal point $F_1$ and a second blurry (e.g., hazy or fuzzy) image created by the focal point $F_2$. However, when the focal points $F_1$ and $F_2$ overlap along the visual axis 120 as depicted in FIGS. 3B and 4B, the patient may visualize two aligned (e.g., coinciding, overlapping) images of the fixation light beam 212 on the retina 116. The two images aligning, overlapping, or coinciding herein refers to the centers of the two images formed by the focal points $F_1$ and $F_2$ spatially aligning, overlapping, or coinciding. Such an alignment happens when the common optical center 314 of the powers 307, 309 of the multifocal lens 308 lie exactly on the visual axis 120 of the eye 100.

Thus, at operation 520, the multifocal lens 308 and/or the patient's head are moved to position the common optical center 314 of the multifocal lens 308 on the visual axis 120 of the eye 100. In the example shown in FIGS. 3A-3B, the multifocal lens 308 coupled to an off-patient device may be moved along the X- and Y-axes in relation to the patient's head while the patient continuously maintains their gaze on the fixation light beam 212 to align the focal point $F_2$ with the focal point $F_1$ on the visual axis 120. Alternatively, the multifocal lens 308 is stationary while the patient moves their head along the X- and Y-axes and continuously maintains their gaze on the fixation light beam 212 in order to try and align or visually overlap the focal point $F_2$ with the focal point $F_1$.

Upon alignment of the focal point $F_2$ with the visual axis 120, the patient sees two overlapping images or spots with spatially coinciding centers. Even while aligned with each other, the first image or spot formed by the focal point F1 is sharp and the second image or spot formed by the focal point F2 is somewhat blurry. As shown in FIG. 3B, when the focal point $F_2$ overlaps with the focal point $F_1$ on the visual axis 120, the line connecting an output point of fixation light source 202 (e.g., origin of the fixation light beam 212) with the common optical center 314 of the multifocal lens 308 intersects the anterior surface of the cornea 104 (e.g., the pupil plane) at the exact X/Y position of the visual axis 120.

Referring now to the embodiments of FIGS. 4A-4C, instead of coupling the multifocal lens 308 to an off-patient device, the multifocal lens 308 is placed in a trial frame 440 that is worn by the patient. In such embodiments, the patient may move (e.g., rotate or tilt up, down, left, and right) their head 460 while wearing the trial frame 440 and continuously maintaining their gaze on the fixation light beam 212 in order to try and align or visually overlap the focal point $F_2$ with the focal point $F_1$ on the visual axis 120.

As shown in FIG. 4A, as the patient focuses their gaze on the fixation light beam 212, a first focal point F1 is formed on the fovea 122. Because the optical center 314 of multifocal lens 308 is not aligned with the visual axis 120, the multifocal lens 308 forms a second focal point $F_2$ within the ocular space of the eye 100 along the optical axis 318 that does not overlap with the visual axis 120. In FIG. 4B, the patient has moved or rotated their head 460 while focusing on the fixation light beam 212 to align the focal point $F_2$ with the focal point $F_1$ on the visual axis 120, thus seeing two images or spots with spatially coinciding centers formed by the fixation light beam 212. As described above, when the focal point $F_2$ overlaps with the focal point $F_1$ on the visual axis 120, the line connecting the fixation light source 202 with the common optical center 314 of the multifocal lens 308 within the trial frame 440 intersects the anterior corneal surface at the location 130 of the visual axis 120.

For purposes of clarity, FIG. 4C illustrates a schematic side view of the patient wearing the multifocal lens 308 when disposed within a trial frame 440. As the patient continuously fixates his gaze on the fixation light beam 212, the patient rotates his or her head 460 in a "yes" (e.g., Y rotational) or "no" (e.g., X rotational) movement. Due to the distance between the patient's eye 100 and the multifocal lens 308, the rotational movement of the patient's head 460 creates displacement of the multifocal lens 308 relative to the patient's eye 100 and the fixation light beam 212. This displacement has the same effect as the movement of the multifocal lens 308 described with reference to FIGS. 3A and 3B. For example, if the distance between the eye 100 and the multifocal lens 308 is 12 mm, and the head is rotated by 5 degrees in either an X or Y movement while the patient maintains their gaze on the fixation light beam 212, the multifocal lens 308 therefore moves (12 mm*tan (5°))=1.05 mm with respect to the eye 100.

Simultaneously with the movement of the patient's head 460 and/or the multifocal lens 308, the imaging camera 204 captures images or video of the multifocal lens 308 and the eye 100 at operation 530. Generally, the imaging camera 204 captures images from a direction along which the fixation light beam 212 travels to the eye 100. In some examples, video recording the eye 100 during the method 500 may increase the accuracy in identifying the location 130 of the visual axis 120. The images or video of the multifocal lens 308 and the eye 100 are then relayed to the image processing system 206, which determines the location of the eye 100 relative to an optical center 314 of the multifocal lens 308 during movement of the patient's head and/or the multifocal lens 308. As described above, determination of the X/Y location of the eye 100 may be accomplished by utilizing the vasculature of the sclera of the eye 100 as landmarks. In some examples, the optical center 314 is designated with crosshair markings 312 on the multifocal lens 308 for identification thereof by the imaging camera 204 and/or image processing system 206.

At operation 540, movement of the patient's head and/or the multifocal lens 308 is continued until the patient reports seeing overlapping images of the fixation light beam 212, such that the centers of the two or more images coincide. Then, at operation 550, the image processing system 206 determines the location 130 of the visual axis 120 of the patient. Generally, the line connecting an output point of fixation light source 202 with the optical center 314 of the multifocal lens 308 will intersect with the outer surface of the cornea 104 at the exact location of the visual axis 120 when the patient visualizes two images with spatially aligned centers and thus, the location 130 of the visual axis 120 may be identified by locating this intersection point.

In some embodiments, a single image of the eye 100 and the multifocal lens 308 is collected by the imaging camera 204 and analyzed by the imaging processing system 206 upon the patient reporting visual overlap of the foci $F_1$ and $F_2$. Thus, the identification of the location 130 of the visual axis 120 may be a singular X, Y coordinate determination. In other embodiments, a video or series of images is collected by the imaging camera 204 and analyzed by the image processing system 206 while the patient attempts to maintain visual overlap of the foci $F_1$ and $F_2$. The video or series of images may be collected over any desired period of time, such as 5 seconds, 10 seconds, 15, seconds, 20 seconds, 25 seconds, or any other suitable period of time. For example, the time period may be between about 5 seconds and about 60 seconds, such as between about 5 seconds and about 30 seconds, such as between about 10 seconds and about 20 seconds. During this time period, the patient is told to try and maintain his/her gaze such that he/she sees overlapping images of the fixation light beam 212. The image processing system 206 may then analyze the video or series of images to determine the average X/Y location of the optical center 314 of the multifocal lens 308 in relation to the X/Y location of the eye 100, thus compensating for any unintended eye and/or head movement of the patient when focusing on the fixation light beam 212. Accordingly, the identification of the location 130 of the visual axis 120 may be an average X/Y coordinate determination.

In some embodiments, the fixation light beam 212 may include two or more wavelengths or ranges of wavelengths having different reflectance characteristics through the multifocal lens 308. In such embodiments, undesired reflection of the fixation light beam 212 toward the imaging camera 204 may be eliminated or significantly reduced during utilization of the visual axis identification system 200. In one example, the fixation light beam 212 may include a first wavelength having a first frequency to which the multifocal lens 308 is highly reflective and to which the imaging camera 204 is insensitive. The fixation light beam 212 may also include a second wavelength having a second frequency that is highly transmissive through the multifocal lens 308 and to which the eye 100 is insensitive and the imaging camera 204 is sensitive. Thus, the fixation light beam 212 may be separated (e.g., filtered) by the multifocal lens 308 such that only light of the second wavelength is transmitted to the imaging camera 204. The spectral separation of the fixation light beam 212 into two or more wavelengths to which the eye 100 and the imaging camera 204 have different sensitivities reduces the disturbing effect of reflection by the multifocal lens 308 and increases the accuracy of visual axis identification system 200 in determining the location 130 of the visual axis 120.

Figure 7A:
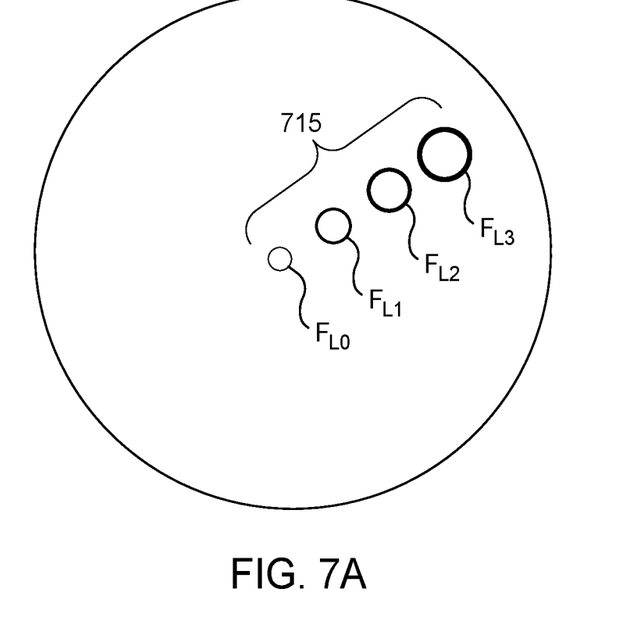
FIG. 7A illustrates the retina of a patient with multiple imaged spots when using the visual axis identification system of FIGS. 6A and 6B, according to certain embodiments of the present disclosure.
Figure 7B:
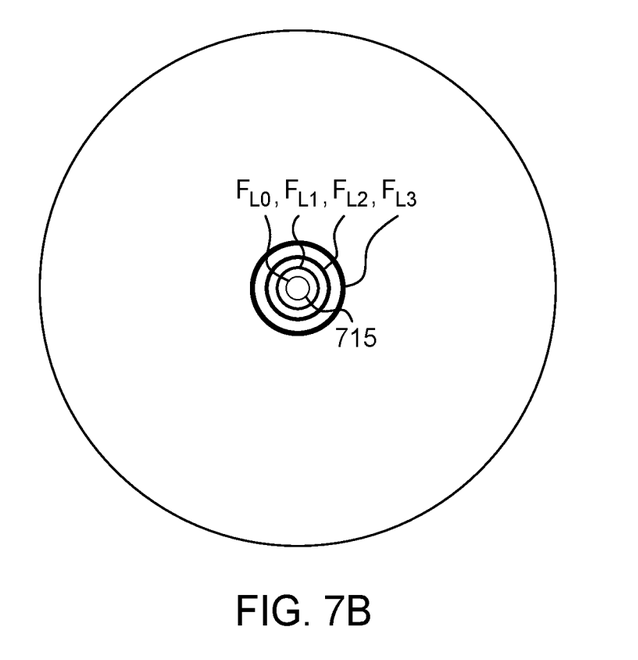
FIG. 7B illustrates the retina of a patient with multiple overlapping imaged spots when using the visual axis identification system of FIGS. 6A and 6B, according to certain embodiments of the present disclosure.

FIGS. 6A-6D illustrate simplified schematic views of an alternative coated multifocal lens 608 that may be used with the visual axis identification system 200 and the method 500, according to some embodiments. FIGS. 7A and 7B illustrate images formed on the retina 116 of a patient while using the coated multifocal lens 608, according to some embodiments. Accordingly, FIGS. 6A-6D and FIGS. 7A and 7B will herein be described together for clarity.

The coated multifocal lens 608 depicted in FIGS. 6A-6D is substantially similar to the multifocal lenses 208 and 308 described above, but includes a coating 603 disposed on two major surfaces 611a, 611b thereof. The coating 603 is partially reflective and partially transmissive of the fixation light beam 212. In some embodiments, the coating 603 enables the spectral separation of the fixation light beam 212 and the light entering the imaging camera 204. For example, the reflectivity peak (e.g., maximum reflectivity) of the coating 603 may correspond with the wavelength of the fixation light beam 212 to be visualized by the patient. In a further example, the coating 603 may have zero reflectivity at the wavelength of the light to be detected by the imaging camera 204. Thus, undesired reflection of the fixation light beam 212 toward the imaging camera 204 may be eliminated or significantly reduced by utilizing the coated multifocal lens 608, enabling more accurate determination of the location 130 of the visual axis 120 during the method 500.

The utilization of the coating 603 on the coated multifocal lens 608 further enables the formation of two or more foci depending on the reflectivity thereof. Generally, the coating 603 enables formation of an infinite number of foci and images, with intensities thereof decreasing according to geometric progression. The human eye 100, however, cannot perceive all of the images, and thus only perceives a limited number thereof. The number of perceivable or visible foci formed can be controlled by modifying the reflectivity characteristics of the coating 603. For clarity, only four foci, $F_{L0}$, $F_{L1}$, $F_{L2}$, and $F_{L3}$ are depicted in FIGS. 6A-6D. When the fixation light beam 212 passes through the coated multifocal lens 608 at a location other than the optical center 614, the multiple foci $F_{L0}$, $F_{L1}$, $F_{L2}$, and $F_{L3}$ are transversally shifted from the optical axis 618 (shown in FIGS. 6A and 6C) and the patient sees non-overlapping spots. However, when the fixation light beam 212 is directed through an optical center 614 of the coated multifocal lens 608 and parallel with the optical axis 618 thereof (shown in FIG. 6D), the foci $F_{L0}$, $F_{L1}$, $F_{L2}$, and $F_{L3}$ visually overlap on the optical axis 618 of the coated multifocal lens 608 and the patient sees overlapping spots.

The multifocal lens 608 may be utilized to locate the visual axis 120 of a patient's eye 100 via substantially similar methods to those described with reference to multifocal lenses 208 and 308 and the method 500. Generally, the multifocal lens 608 is transversally moved in an X or Y direction relative to the patient's eye 100 as the patient continuously focuses on the fixation light beam 212. When the patient visualizes overlapping spots with spatially coinciding centers, the fixation light beam 212 is being directed through the optical center 614 of the multifocal lens 608 and the optical center 614 lies exactly on the visual axis 120 of the eye 100, thereby enabling identification of the visual axis 120.

FIG. 7A depicts the patient's view when looking at the fixation light beam 212 through an off-center location of the coated multifocal lens 608. There, the foci $F_{L0}$, $F_{L1}$, $F_{L2}$, and $F_{L3}$ are unaligned on both the optical axis 618 and the visual axis 120. The patient sees a substantially linear row of spots 715 varying in size and sharpness. FIG. 7B depicts what a patient may see when the fixation light beam 212 passes through the optical center 614 of the coated multifocal lens 608. The foci $F_{L0}$, $F_{L1}$, $F_{L2}$, and $F_{L3}$ are visually overlapping with each other on the optical axis 618 and the visual axis 120. The utilization of a lens forming two or more foci for alignment during the method 500 enables a more precise and accurate determination of the location of the visual axis 120 as compared to a lens forming a single focal point.

The methods and apparatus described above provide a novel visual axis identification system that may be utilized to improve the efficacy of ophthalmic procedures, such as presbyopic treatments including the fitting of corrective lenses, refractive surgery, artificial lens implants, and multifocal corneal inlays. The described visual axis identification systems may further be utilized in combination with any suitable ophthalmic diagnostic devices. Examples of suitable diagnostic devices include corneal topographers, optical coherence tomographers, wavefront meters (e.g., aberrometers), image-guided biometers, surgical microscopes, and other image-based diagnostic devices. In some examples, the visual axis identification system 200 may be utilized in combination with the CENTURION®, INFINITI™, Verion™, ORA™ System, LenSx®, LuxOR™ LX3 platforms manufactured by Alcon, Fort Worth, Texas. In some examples, the visual axis identification system 200 may be utilized with ophthalmic platforms provided by other manufactures.

EXAMPLE EMBODIMENTS

Embodiment 1

A method for determining a location of a visual axis of a patient's eye, comprising placing a multifocal optical lens adjacent to the patient's eye, the multifocal optical lens comprising two or more optical powers with corresponding spatially coinciding optical centers at an optical center of the multifocal optical lens; generating and directing a fixation light towards the patient's eye, the fixation light forming two or more images at focal points near a retina of the patient's eye, the two or more images corresponding to the two or more optical powers of the multifocal optical lens; capturing images of the patient's eye and the multifocal optical lens along a direction of the fixation light; determining an X/Y location of the patient's eye relative to an X/Y location of the optical center of the multifocal optical lens; moving the multifocal optical lens with respect to the patient's eye while the patient maintains their gaze on the fixation light until centers of the two or more images coincide in a view of the patient; and identifying the location of the visual axis of the patient's eye at a pupil plane of the patient's eye, the location of the visual axis corresponding with a location of the optical center of the multifocal optical lens as viewed from the direction of the fixation light.

Embodiment 2

The method of Embodiment 1, wherein the multifocal optical lens is coupled to a trial frame worn by the patient.

Embodiment 3

The method of Embodiment 1, wherein the multifocal optical lens is coupled to an off-patient device.

Embodiment 4

A system for determining a location of a visual axis of a patient's eye, comprising a multifocal optical lens; a detector configured to track movement of the eye, the detector further configured to capture images of the multifocal optical lens in relation to a location of the eye; and a processing system configured to identify the location of the visual axis of the eye at an anterior surface of the eye based on the images captured by the detector, wherein the visual axis of the eye corresponds to an optical center of the multifocal optical lens when centers of two or more focal points of the multifocal optical lens coincide in a view of the patient.

Embodiment 5

The system of Embodiment 4, wherein the multifocal optical lens is coupled to a trial frame.

Embodiment 6

The system of Embodiment 4, wherein the multifocal optical lens is coupled to an off-patient device.

Embodiment 7

The system of Embodiment 4, wherein the detector is an infrared camera.

Embodiment 8

The system of Embodiment 7, wherein the infrared camera is configured to track movement of the eye by detecting landmarks of vasculature in a sclera of the eye.

Embodiment 9

The system of Embodiment 4, wherein the multifocal optical lens comprises an axicon.

While the foregoing is directed to embodiments of the present disclosure, other and further embodiments of the disclosure may be devised without departing from the basic scope thereof, and the scope thereof is determined by the claims that follow.

What is claimed is:

1. A method for determining a location of a visual axis of a patient's eye, comprising:
    placing a multifocal optical lens adjacent to the patient's eye, the multifocal optical lens comprising two or more optical powers with corresponding spatially coinciding optical centers at an optical center of the multifocal optical lens;
    generating and directing a fixation light towards the patient's eye, the fixation light forming two or more images at focal points near a retina of the patient's eye, the two or more images corresponding to the two or more optical powers of the multifocal optical lens;
    capturing images of the patient's eye and the multifocal optical lens along a direction of the fixation light;
    determining an X/Y location of the patient's eye relative to an X/Y location of the optical center of the multifocal optical lens;
    moving the multifocal optical lens with respect to the patient's eye while the patient maintains their gaze on the fixation light until centers of the two or more images coincide in a view of the patient; and
    identifying the location of the visual axis of the patient's eye at a pupil plane of the patient's eye, the location of the visual axis corresponding with a location of the optical center of the multifocal optical lens as viewed from the direction of the fixation light.

2. The method of claim 1, wherein the multifocal optical lens comprises an optical coating on two or more surfaces thereof.

3. The method of claim 2, wherein the multifocal optical lens is configured to form more than two foci within the patient's eye.

4. The method of claim 1, wherein the location of the visual axis further corresponds with the location of the optical center of the multifocal optical lens when the centers of the two or more images coincide with one another in the view of the patient.

5. The method of claim 1, wherein the fixation light is spectrally separated into two or more wavelength ranges having different refractivity and reflectivity characteristics through the multifocal optical lens.

6. The method of claim 1, wherein the optical center of the multifocal optical lens is marked by a crosshair marking.

7. The method of claim 1, wherein identifying the location of the visual axis of the patient's eye further comprises:
    spatially averaging an X/Y location of the optical center of the multifocal optical lens in relation to the location of the patient's eye during a time period in which the patient maintains their gaze on the fixation light such that the patient sees the coinciding images formed by the fixation light.

8. The method of claim 7, wherein the time period is between about 5 seconds and about 60 seconds.

9. The method of claim 1, wherein the multifocal optical lens is a complex diffractive optical element configured to form a hyperlong focal line.

10. The method of claim 9, wherein the multifocal optical lens comprises an axicon.

11. The method of claim 9, wherein the multifocal optical lens comprises an aspheric extended depth of focus lens.

12. A system for determining a location of a visual axis of a patient's eye, comprising:
    a multifocal optical lens;
    a detector configured to track movement of the eye, the detector further configured to capture images of the multifocal optical lens in relation to a location of the eye; and
    a processing system configured to identify the location of the visual axis of the eye at an anterior surface of the eye based on the images captured by the detector, wherein the visual axis of the eye corresponds to an optical center of the multifocal optical lens when centers of two or more focal points of the multifocal optical lens coincide and form overlapping images in a view of the patient.

13. The system of claim 12, wherein the multifocal optical lens is a complex diffractive optical element configured to form a hyperlong focal line.

14. The system of claim 13, wherein the multifocal optical lens comprises an aspheric extended depth of focus lens.

15. The system of claim 12, wherein the processing system being configured to identify the location of the visual axis of the eye comprises the processing system being configured to:
    average an X/Y location of the optical center of the multifocal optical lens in relation to the location of the eye during a time period in which a patient maintains their gaze on a fixation light such that the patient sees overlapping images formed by the fixation light.

* * * * *